(12) United States Patent
Kito (10) Patent No.: US 7,977,644 B2
(45) Date of Patent: Jul. 12, 2011

(54) PORTABLE RADIATION DETECTOR

(75) Inventor: Eiichi Kito, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/540,385

(22) Filed: Aug. 13, 2009

(65) Prior Publication Data
US 2010/0044575 A1 Feb. 25, 2010

(30) Foreign Application Priority Data

Aug. 20, 2008 (JP) ................................. 2008-211785

(51) Int. Cl.
*G01T 1/24* (2006.01)

(52) U.S. Cl. ................................................. 250/370.09

(58) Field of Classification Search ............. 250/370.09, 250/580, 581
See application file for complete search history.

(56) References Cited

U.S. PATENT DOCUMENTS

| 4,980,945 | A | * | 1/1991 | Bewley ........................... 15/339 |
| 5,514,873 | A | | 5/1996 | Schulze-Ganzlin et al. |
| 5,844,961 | A | * | 12/1998 | McEvoy et al. .............. 378/98.8 |
| 6,296,386 | B1 | * | 10/2001 | Heidsieck et al. ............ 378/189 |
| 2003/0165237 | A1 | * | 9/2003 | Farr et al. ...................... 379/430 |
| 2004/0036449 | A1 | * | 2/2004 | Bean et al. ..................... 320/166 |
| 2004/0114725 | A1 | * | 6/2004 | Yamamoto ..................... 378/189 |
| 2006/0202127 | A1 | * | 9/2006 | Ozeki ....................... 250/370.01 |
| 2007/0173108 | A1 | * | 7/2007 | Niwa ............................. 439/497 |

FOREIGN PATENT DOCUMENTS

| JP | 2005-006979 A | 1/2005 |
| JP | 2007-044068 A | 2/2007 |

* cited by examiner

*Primary Examiner* — David P Porta
*Assistant Examiner* — Marcus H Taningco
(74) *Attorney, Agent, or Firm* — Solaris Intellectual Property Group, PLLC (57) ABSTRACT

There is provided a portable radiation detector including: a housing; a wireless communication section accommodated in the housing, and carrying out wireless communication of image data of a detected radiation image; a cable whose one end portion is connected to the housing; a connector provided at another end portion of the cable, and able to be connected to an external device; and a connector holding mechanism provided at the housing, and holding the connector removably at the housing.

8 Claims, 13 Drawing Sheets

PORTABLE RADIATION DETECTOR

CROSS-REFERENCE TO RELATED APPLICATION

This application is based on and claims priority under 35 USC 119 from Japanese Patent Application No. 2008-211785 filed on Aug. 20, 2008, the disclosure of which is incorporated by reference herein.

BACKGROUND OF THE INVENTION

1. Field of the Invention

The present invention relates to a portable radiation detector that can be carried.

2. Description of the Related Art

A wireless electronic cassette is known as a portable radiation detector. (Refer to U.S. Pat. No. 5,514,873.)

Here, "wireless" means able to communicate and able to be charged without using a cable. "Wireless communication" of course includes communication and charging by setting a radiation detector in a cradle and connecting the respective connectors thereof.

Further, Japanese Patent Applications Laid-Open (JP-A) Nos. 2005-6979 and 2007-44068 disclose electronic cassettes having the function of switching between wireless communication and wired communication, and that the ease of handling improves by switching between wired and wireless depending on the charged amount or the state of communication.

In the electronic cassettes that have cables for supplying electric power that are disclosed in U.S. Pat. No. 5,514,873 and JP-A Nos. 2005-6979 and 2007-44068, the cables are only used for connection to a charging device. Electronic cassettes to which electric power is supplied by a cable do not have the same operability as wireless electronic cassettes (e.g., electronic cassettes that are charged merely by being set in a cradle).

SUMMARY OF THE INVENTION

In view of the above-described circumstances, the present invention facilitates handling of a portable radiation detector that has a cable.

A portable radiation detector relating to an aspect of the present invention includes: a housing; a wireless communication section accommodated in the housing, and carrying out wireless communication of image data of a detected radiation image; a cable whose one end portion is connected to the housing; a connector provided at another end portion of the cable, and able to be connected to an external device; and a connector holding mechanism provided at the housing, and holding the connector removably at the housing.

BRIEF DESCRIPTION OF THE DRAWINGS

An exemplary embodiment of the present invention will be described in detail based on the following figures, wherein.

DETAILED DESCRIPTION OF THE INVENTION

Structure of Electronic Cassette Relating to Present Exemplary Embodiment

Figure 1:
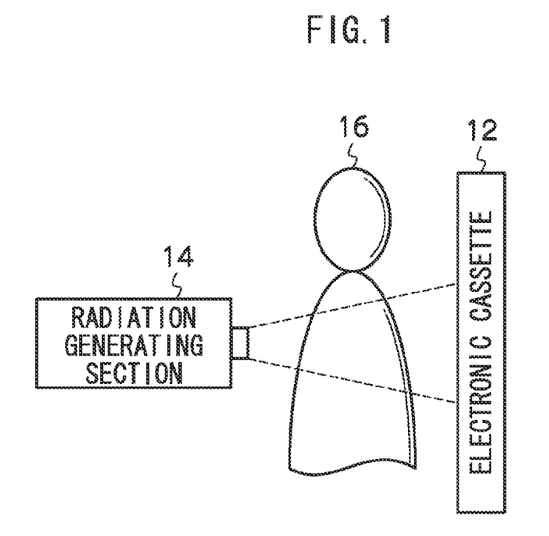
FIG. 1 is a schematic drawing showing the placement of an electronic cassette at the time of photographing a radiation image.
Figure 2:
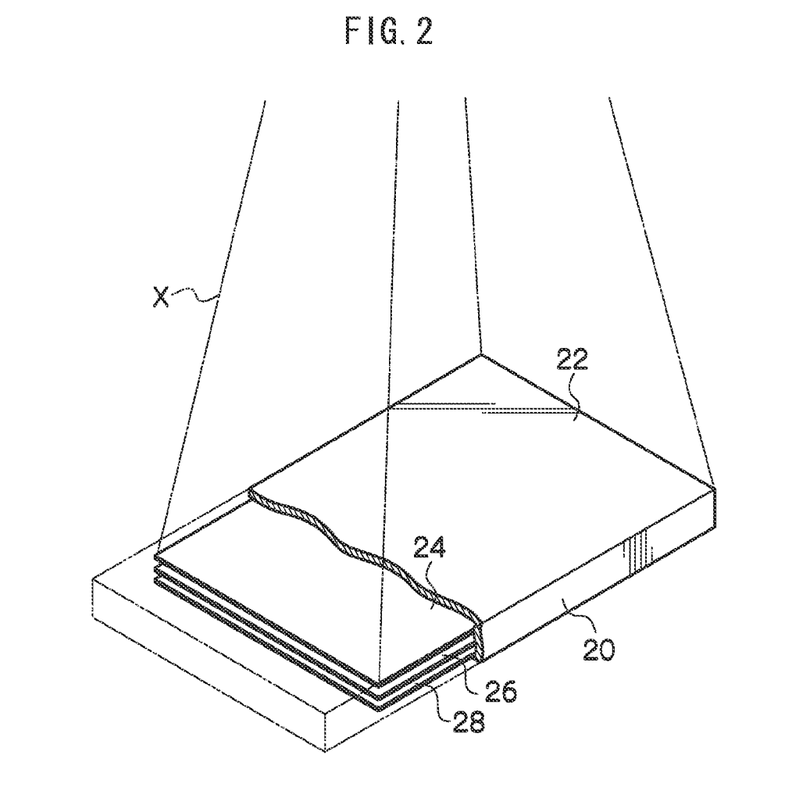
FIG. 2 is a schematic perspective view showing the internal structure of the electronic cassette.
Figure 3:
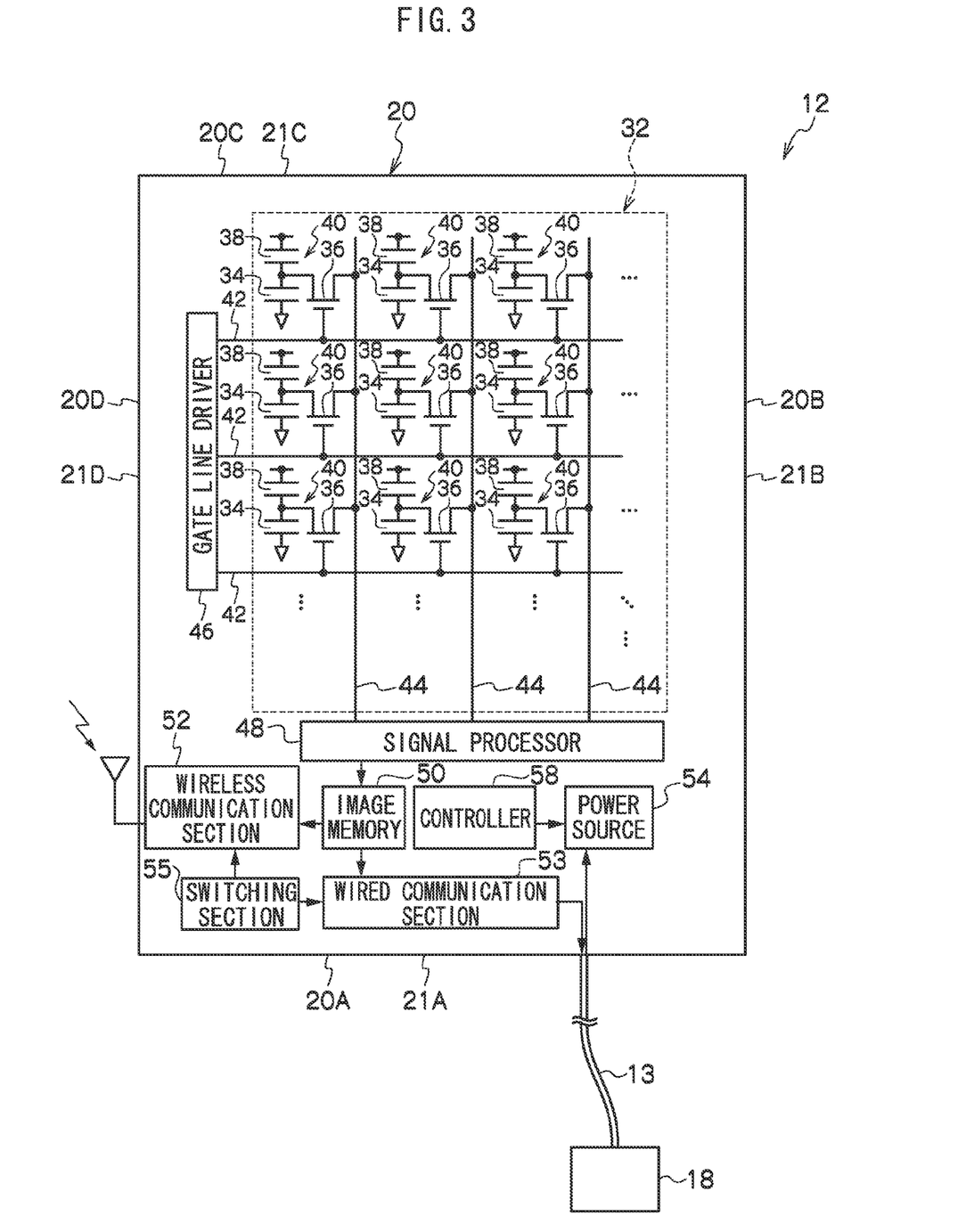
FIG. 3 is a block diagram schematically showing the schematic structure of the electronic cassette.

First, the structure of an electronic cassette, that serves as an example of a portable radiation detector, will be described. FIG. 1 is a schematic drawing showing the placement of the electronic cassette at the time of photographing a radiation image. FIG. 2 is a schematic perspective view showing the internal structure of the electronic cassette. FIG. 3 is a block diagram schematically showing the schematic structure of the electronic cassette.

An electronic cassette 12 relating to the present exemplary embodiment is a radiation photographing device that is portable, and detects radiation from a radiation source that has been transmitted through a photographic subject, and generates image information of a radiation image that is expressed by the detected radiation, and can store the generated image information. The electronic cassette 12 is concretely structured as follows. Note that the electronic cassette 12 may be a structure that does not store generated image information.

As shown in FIG. 1, at the time of photographing a radiation image, the electronic cassette 12 is disposed such that there is a space between the electronic cassette 12 and a radiation generating section 14 that serves as a radiation source that generates radiation. The region between the radiation generating section 14 and the electronic cassette 12 at this time is a photographing region at which a subject 16, the photographic subject, is positioned. When photographing of a radiation image is instructed, the radiation generating section 14 emits radiation with an amount of radiation set by photographing conditions and the like that are provided in advance.

The radiation that is emitted from the radiation generating section 14 carries image information by being transmitted through the subject 16 who is positioned at the photographing position, and thereafter, is irradiated onto the electronic cassette 12.

As shown in FIG. 2, the electronic cassette 12 has a flat-plate-shaped housing 20 that is formed of a material through which radiation X can be transmitted, and that has a predetermined thickness. A grid 24, a radiation detecting panel 26 and a lead plate 28 are accommodated within the housing 20 in that order from an irradiation surface 22 side of the housing 20 at which the radiation X is irradiated. The grid 24 removes scattered radiation of the radiation X that arises as the radiation is transmitted through the subject 16. The radiation detecting panel 26 is an example of a radiation detector that detects radiation from the radiation generating section 14 that has passed through the subject 16. The lead plate 28 absorbs the back-scattered radiation of the radiation X.

The radiation detecting panel 26 of the electronic cassette 12 is structured such that a photoelectric converting layer, that absorbs radiation and converts it into charges, is layered on a TFT active matrix substrate 32 shown in FIG. 3. The photoelectric converting layer is formed from, for example, an amorphous a-Se (amorphous selenium) whose main component is selenium (e.g., a content of greater than or equal to 50%). When radiation is irradiated, the photoelectric converting layer generates, at the interior thereof, charges (electron-hole pairs) of a charge amount corresponding to the irradiated radiation amount, and thereby converts the irradiated radiation into charges.

Note that, instead of an X-ray—charge converting material such as amorphous selenium that directly converts the radiation X into charges, the radiation detecting panel 26 may convert the radiation X into charges indirectly by using a fluorescent material and photoelectric converting elements (photodiodes). Gadolinium oxysulfide (GOS) and cesium iodide (CsI) are well known as fluorescent materials. In this case, conversion from X-rays into light is carried out by the fluorescent material, and the conversion from light into charges is carried out by the photodiodes that are photoelectric converting elements.

Further, numerous pixel portions 40 are arranged in the form of a matrix on the TFT active matrix substrate 32. (In FIG. 3, the photoelectric converting layer corresponding to the individual pixel portions 40 is shown schematically as photoelectric converting portions 38.) The pixel portion 40 has a storage capacitor 34 that accumulates charges generated at the photoelectric converting layer, and a TFT 36 for reading-out the charges accumulated in the storage capacitor 34. The charges, that are generated at the photoelectric converting layer accompanying the irradiation of radiation onto the electronic cassette 12, are accumulated in the storage capacitors 34 of the individual pixel portions 40. Due thereto, a radiation image, that is expressed by the radiation that has been transmitted through the photographic subject and irradiated onto the electronic cassette 12, is converted into image information in accordance with charges, and is held at the radiation detecting panel 26.

Gate lines 42 and data lines 44 are provided at the TFT active matrix substrate 32. The gate lines 42 are plural lines that extend in a given direction (the row direction) and are for turning the TFTs 36 of the individual pixel portions 40 on and off. The data lines 44 are plural lines that extend in a direction (the column direction) orthogonal to the gate lines 42 and are for reading-out the accumulated charges from the storage capacitors 34 via the TFTs 36 that have been turned on. The individual gate lines 42 are connected to a gate line driver 46, and the individual data lines 44 are connected to a signal processor 48.

When charges are accumulated in the storage capacitors 34 of the individual pixel portions 40, the TFTs 36 of the individual pixel portions 40 are turned on in order in units of rows by signals supplied from the gate line driver 46 via the gate lines 42. The charges, that are accumulated in the storage capacitors 34 of the pixel portions 40 whose TFTs 36 have been turned on, are transferred through the data lines 44 as charge signals and are inputted to the signal processor 48. Accordingly, the charges, that are accumulated in the storage capacitors 34 of the individual pixel portions 40, are read-out in order in units of rows.

The signal processor 48 is equipped with an amplifier and a sample/hold circuit that are provided for each of the individual data lines 44. The charge signals that are transferred through the individual data lines 44 are amplified at the amplifiers, and thereafter, are held in the sample/hold circuits. Further, multiplexers and A/D converters 48A, that serve as an example of an electric signal converter that converts the charge signals into electric signals that carry image information, are connected in that order to the output sides of the sample/hold circuits. The charge signals, that are held in the individual sample/hold circuits, are inputted in order (serially) to the multiplexers, and analog electric signals are converted into digital electric signals by the A/D converters 48A. An image memory 50 is connected to the signal processor 48. The image information, that are outputted from the A/D converters 48A of the signal processor 48, are stored in order in the image memory 50. The image memory 50 has a storage capacity that can store image information of plural frames. Each time photographing of a radiation image is carried out, the image information obtained by photographing is successively stored in the image memory 50.

The electronic cassette 12 has a wireless communication section 52 and a controller 58. The wireless communication section 52 transmits and receives image data of radiation images wirelessly to and from a display device. The controller 58 is an example of a controller that controls the radiation detecting panel 26, and controls all of the operations of the device.

The wireless communication section 52 has an antenna for transmitting and receiving radio waves, and the transmission and reception of image data is carried out via the antenna.

Note that the display device has a PC (personal computer) that includes a keyboard and mouse serving as inputs, a display, a CPU, a ROM, a RAM, and the like. The display device also has a communication section for carrying out transmission and reception of data to and from the electronic cassette 12.

The controller 58 has a microcomputer that includes a CPU that governs control of the electronic cassette 12 overall, a ROM serving as a storage medium that stores various types of processing programs, a RAM serving as a work area that temporarily stores data, and a memory serving as a storage in which various types of information is stored, and the like.

Note that the controller 58 is not limited to controlling the operations of the entire device, and may control the operations of some of the structural parts of the device.

The electronic cassette 12 has a power source 54. The power source 54 supplies electric power to at least some of the structural parts including the radiation detecting panel 26, and supplies electric power to structural parts such as various types of circuits and elements in order to operate the electronic cassette 12.

The power source 54 has a battery (a chargeable secondary battery), that serves as a power storage that stores electric power to be supplied by the power source 54, so that the portability of the electronic cassette 12 is not adversely affected.

The power storage that stores the electric power to be supplied by the power source 54 is not limited to a chargeable secondary battery. A nickel-hydrogen battery, a lithium ion battery, a lead storage battery, a capacitor, or the like may be used.

Further, the power source is not limited to a structure that supplies electric power to the structural parts of the entire device as in the present exemplary embodiment, and may supply electric power to some of the structural parts of the device. Further, the electronic cassette 12 may be structured so as to have plural power sources.

Shape of Housing 20 of Electronic Cassette 12, and Cable Connected to Housing 20

The shape of the housing 20 of the electronic cassette 12, and the cable that is connected to the housing 20, will be described next.

As shown in FIG. 3, the housing 20 of the electronic cassette 12 is a shape that, in plan view, i.e., as seen from the side onto which radiation is irradiated (the side at which the subject 16 is positioned), has four sides (four straight lines) 21A, 21B, 21C, 21D at the outer edges thereof, and specifically, forms a quadrilateral shape (quadrangular shape). More specifically, the housing 20 of the electronic cassette 12 is rectangular. Note that the electronic cassette 12 may be a shape at which the corners are rounded.

A side surface 20A that surfaces the side 21A, a side surface 20B that structures the side 21B, a side surface 20C that structures the side 21C, and a side surface 20D that structures the side 21D are formed at the housing 20.

Further, the TFT active matrix substrate 32 (detecting region) as well is formed similarly to the shape of the electronic cassette 12, and is a shape that, in plan view, i.e., as seen from the side onto which radiation is irradiated (the side at which the subject 16 is positioned), has four sides (four straight lines) at the outer edges thereof, and specifically, forms a quadrilateral shape (quadrangular shape). More specifically, the TFT active matrix substrate 32 (the detecting region) is rectangular.

Further, as shown in FIG. 3, a cable 13 is connected to the housing 20 of the electronic cassette 12.

One end portion of the cable 13 is fixedly connected to the housing 20, and the cable 13 is structured such that it cannot be removed from the housing 20. Note that the cable 13 may be structured so as to be removably connected to the housing 20.

The one end portion of the cable 13 is electrically connected to the power source 54. Due thereto, electric power can be supplied to the battery of the power source 54 via the cable 13.

In the present exemplary embodiment, the cable 13 is also used as a cable for wired communication of image data. The one end portion of the cable 13 is electrically connected also to a wired communication section 53. A switching section 55, for switching the form of communication to either wireless or wired, is connected to the wired communication section 53 and the wireless communication section 52.

Due to wireless communication being selected by the switching section 55, the transmission and reception of image data through the antenna of the wireless communication section 52 becomes possible. Further, due to wired communication being selected by the switching section 55, the transmission and reception of image data from the wired communication section 53 through the cable 13 becomes possible.

Figure 4:
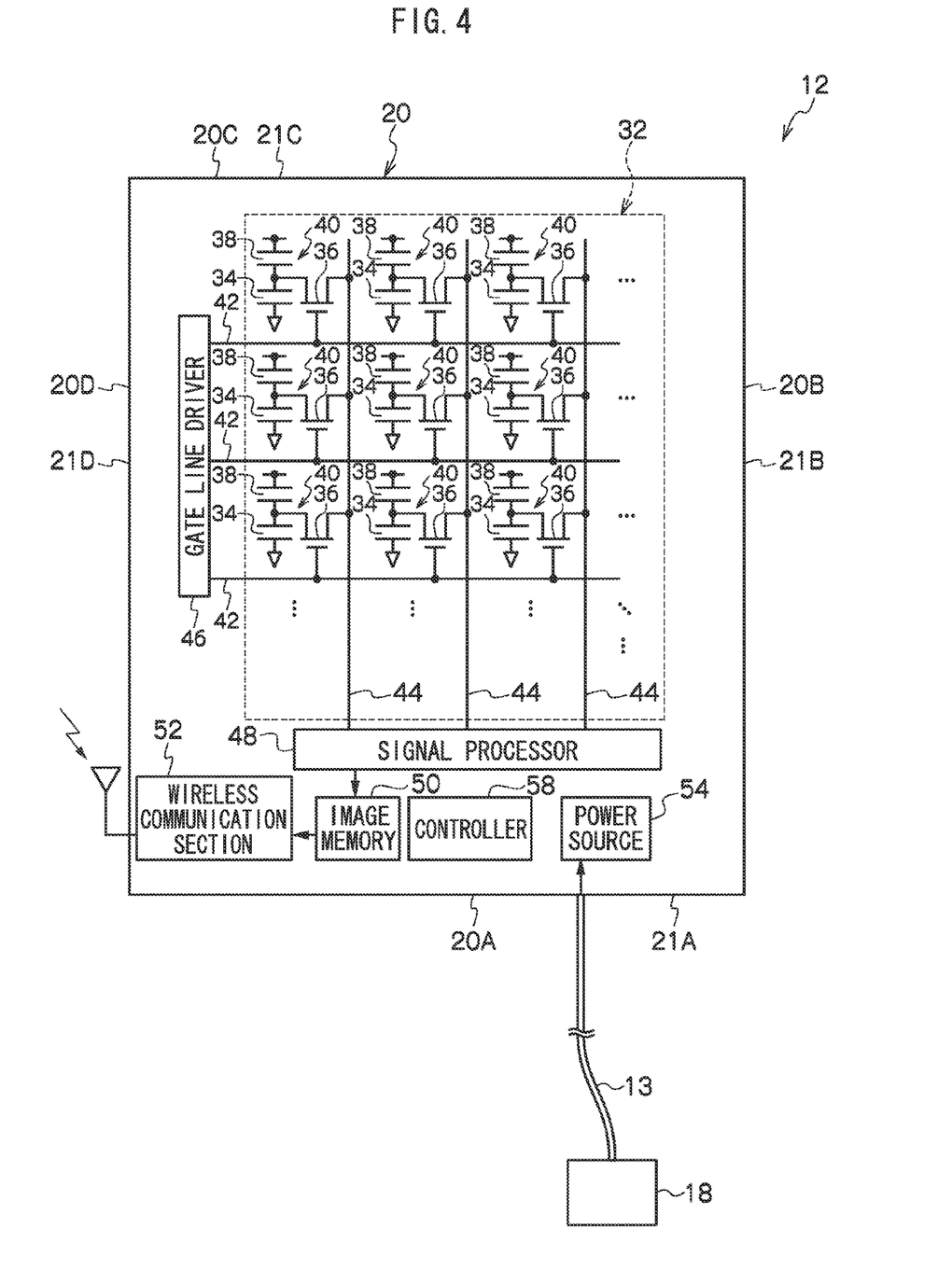
FIG. 4 is a block diagram schematically showing the structure of an electronic cassette relating to a modified example that does not have a wired communication section.

Note that the cable 13 is not limited to a structure that is used both for charging the power source 54 and for wired communication. As shown in FIG. 4, the electronic cassette 12 may be structured so as to not have the wired communication section 53, and the cable 13 may be connected electrically to only the power source 54.

Figure 5:
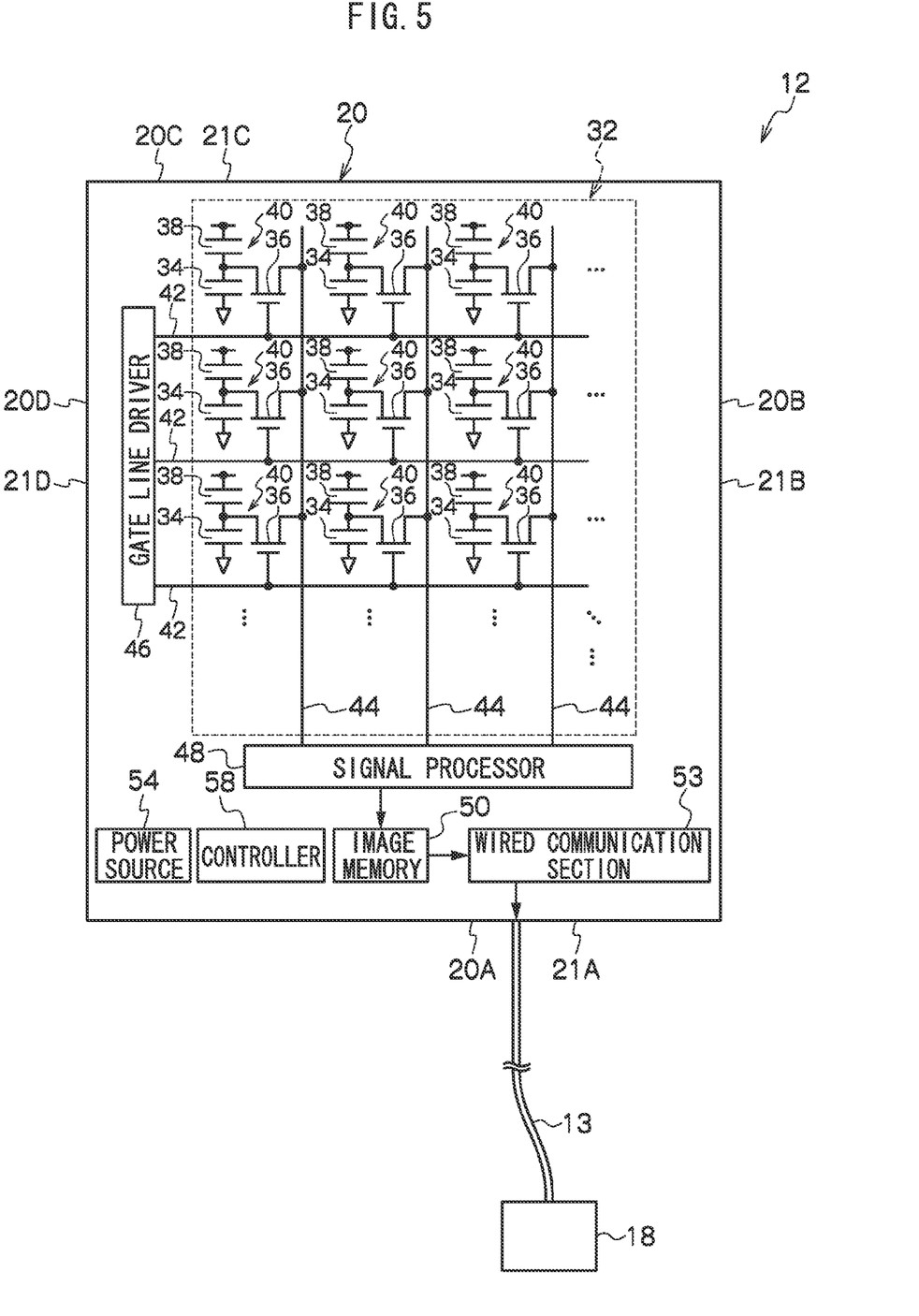
FIG. 5 is a block diagram schematically showing the structure of an electronic cassette relating to a modified example in which a cable is connected only to a wired communication section.

Further, as shown in FIG. 5, the cable 13 may be structured so as to be electrically connected only to the wired communication section 53, without being connected to the power source 54.

As shown in FIG. 3, a connector 18, that can be connected to a first power supply device 100 (see FIG. 8) and a second power supply device 200 (see FIG. 9) that are examples of external devices, is provided at the other end portion of the cable 13.

Figure 6:
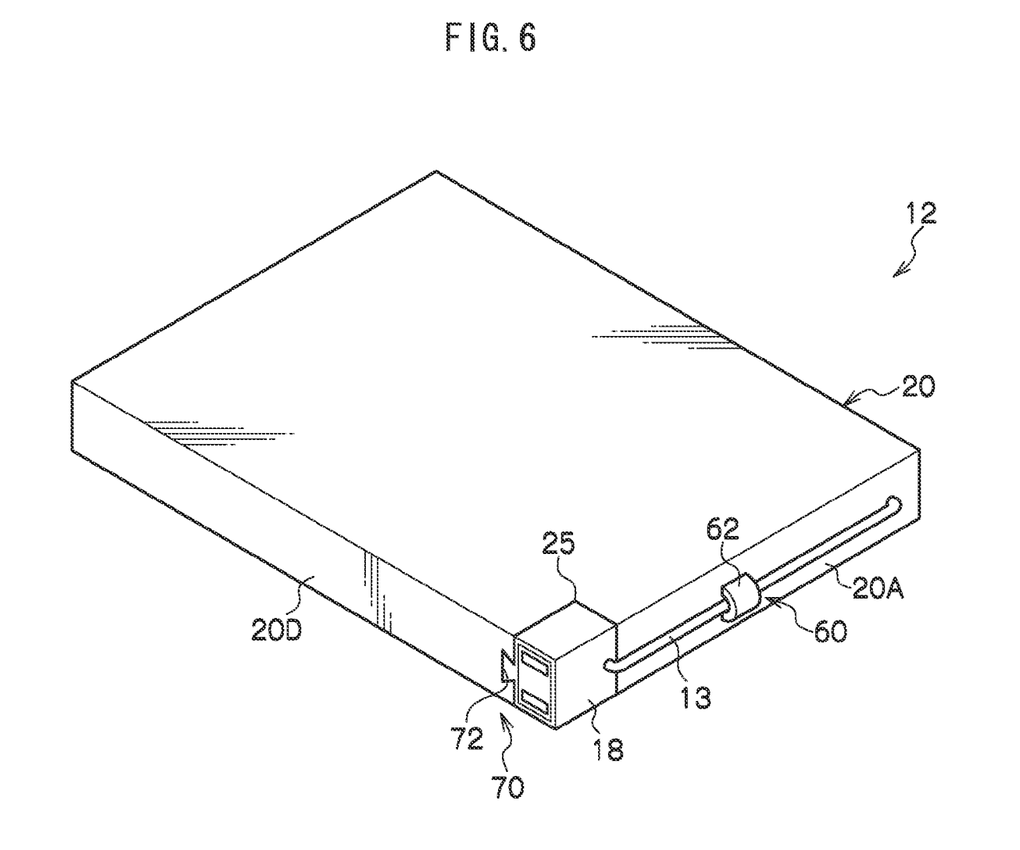
FIG. 6 is a schematic perspective view showing a structure that holds a connector at a housing.
Figure 7:
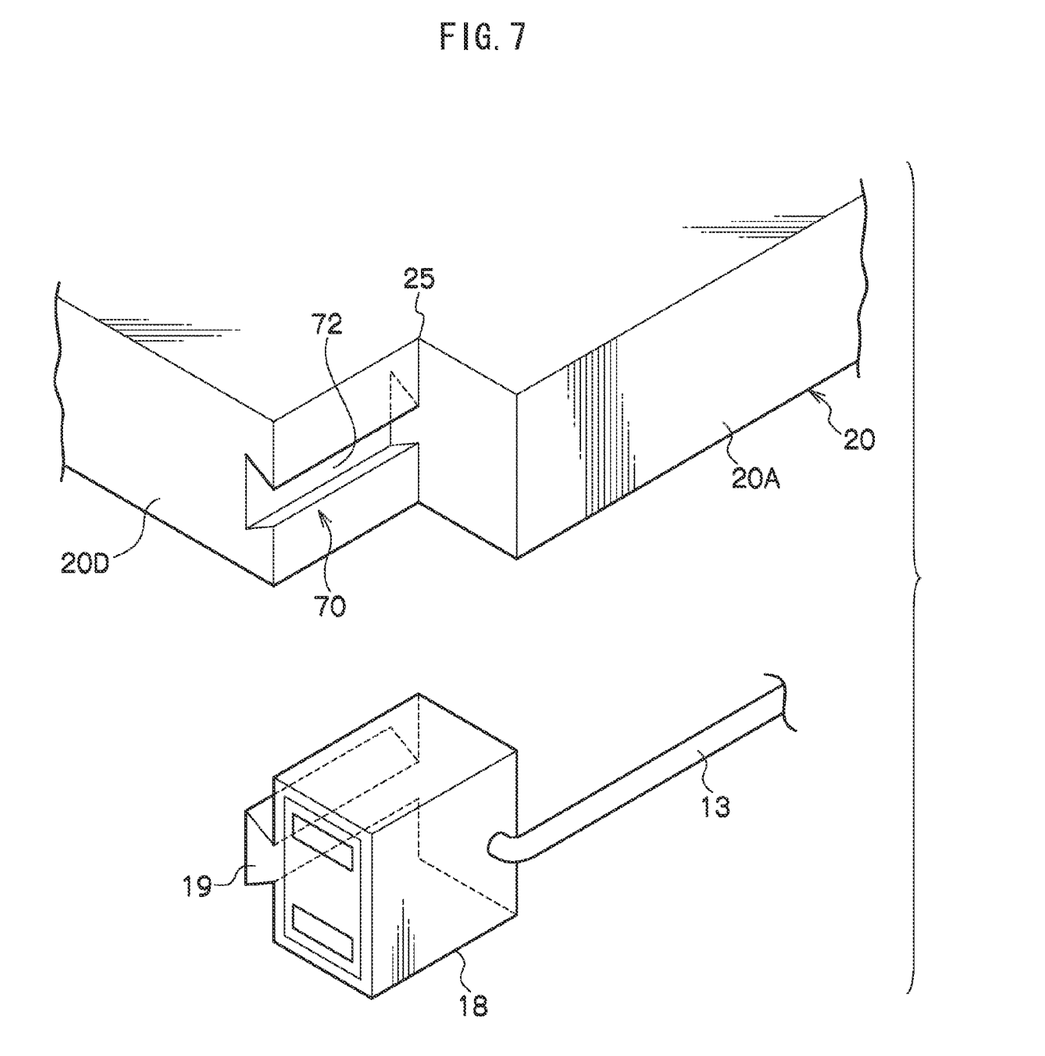
FIG. 7 is an enlarged view showing, in an enlarged manner, a holding mechanism that holds the connector at the housing.

As shown in FIG. 6 and FIG. 7, a holding mechanism 70 that holds the connector 18 is provided at a corner portion 25 of the housing 20 wherein corner portion 25 is formed by the side surface 20A and the side surface 20D. The holding mechanism 70 is structured to have a groove 72 that is formed in the housing 20. A projection 19, that is inserted in the groove 72, is formed at the connector 18.

Due to the projection 19 being inserted in the groove 72, the connector 18 is held at the housing 20 so as to be able to be removed from the housing 20. In the state in which the connector 18 is held at the housing 20, the shape of the housing 20 including the connector 18 is rectangular. Accordingly, the shape of the housing 20 excluding the connector 18 is a rectangular shape from which a portion is cut-out.

Note that the holding mechanism 70 is not limited to the above-described structure, and can be made to be any of various structures. For example, the holding mechanism 70 may be structured such that the connector 18 is removably held at the housing 20 by using a holding member such as a snap-fit or the like.

Figure 8:
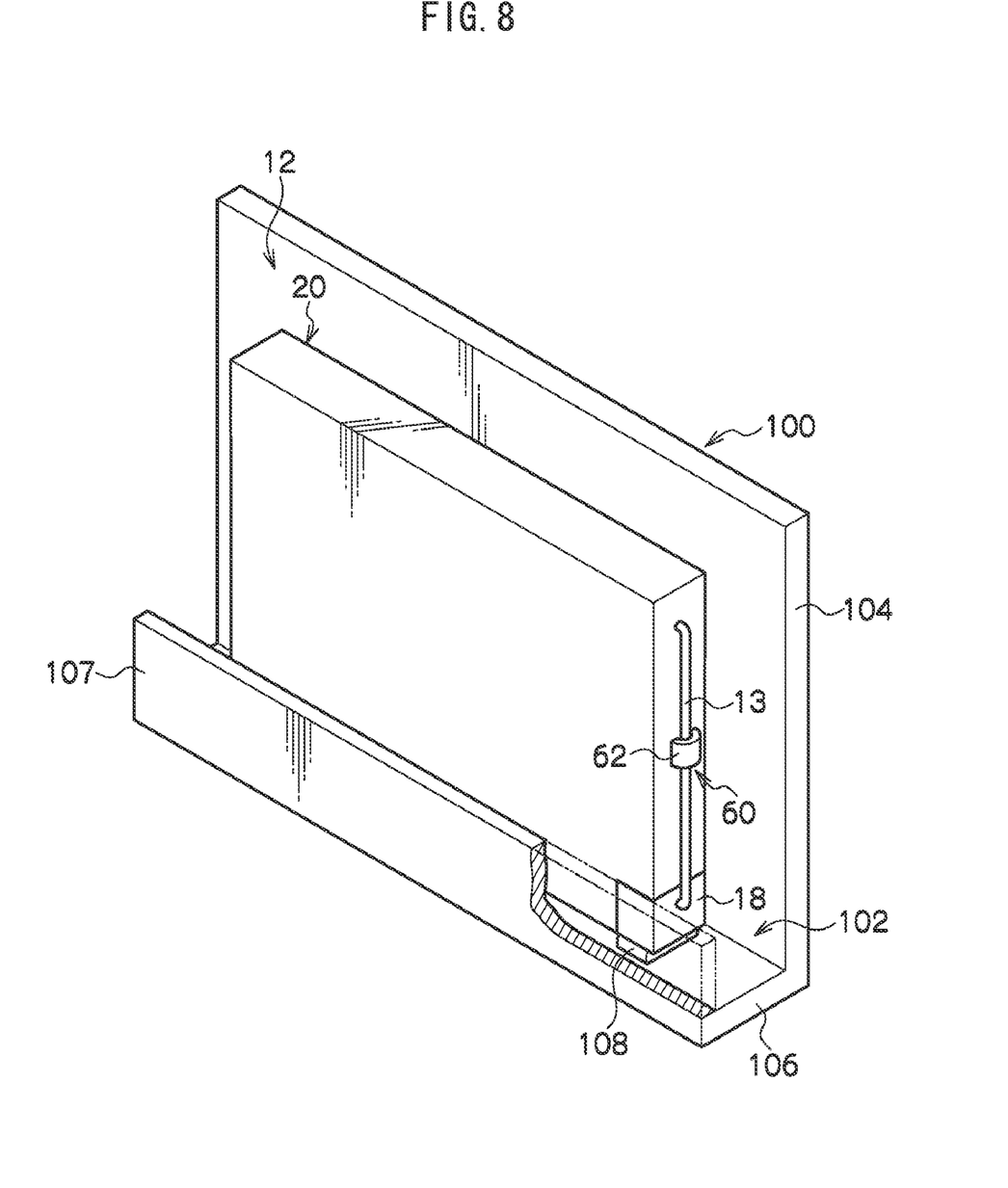
FIG. 8 is a schematic perspective view showing a state in which the connector is connected to a first power supply device.

As shown in FIG. 8, at the electronic cassette 12, the housing 20, that is in a state in which the connector 18 is held thereat, can be set in the first power supply device 100. The first power supply device 100 has an accommodating portion 102 that is surrounded by a back surface 104, a floor surface 106 and a front surface 107. The housing 20 of the electronic cassette 12 is accommodated in the accommodating portion 102, and is set in the first power supply device 100.

A connector 108, that is electrically connected to the connector 18, is provided at an opposing surface that opposes the connector 18 of the housing 20 that is set in the first power supply device 100. The housing 20 is set in the first power supply device 100 in a state in which the held connector 18 faces downward. Specifically, the connector 108 is provided at the floor surface of the first power supply device 100.

Due thereto, as shown in FIG. 8, by setting the housing 20 in the first power supply device 100, the connector 18 of the electronic cassette 12 and the connector 108 of the first power supply device 100 are connected, and the power source 54 of the electronic cassette 12 can be charged.

Figure 9:
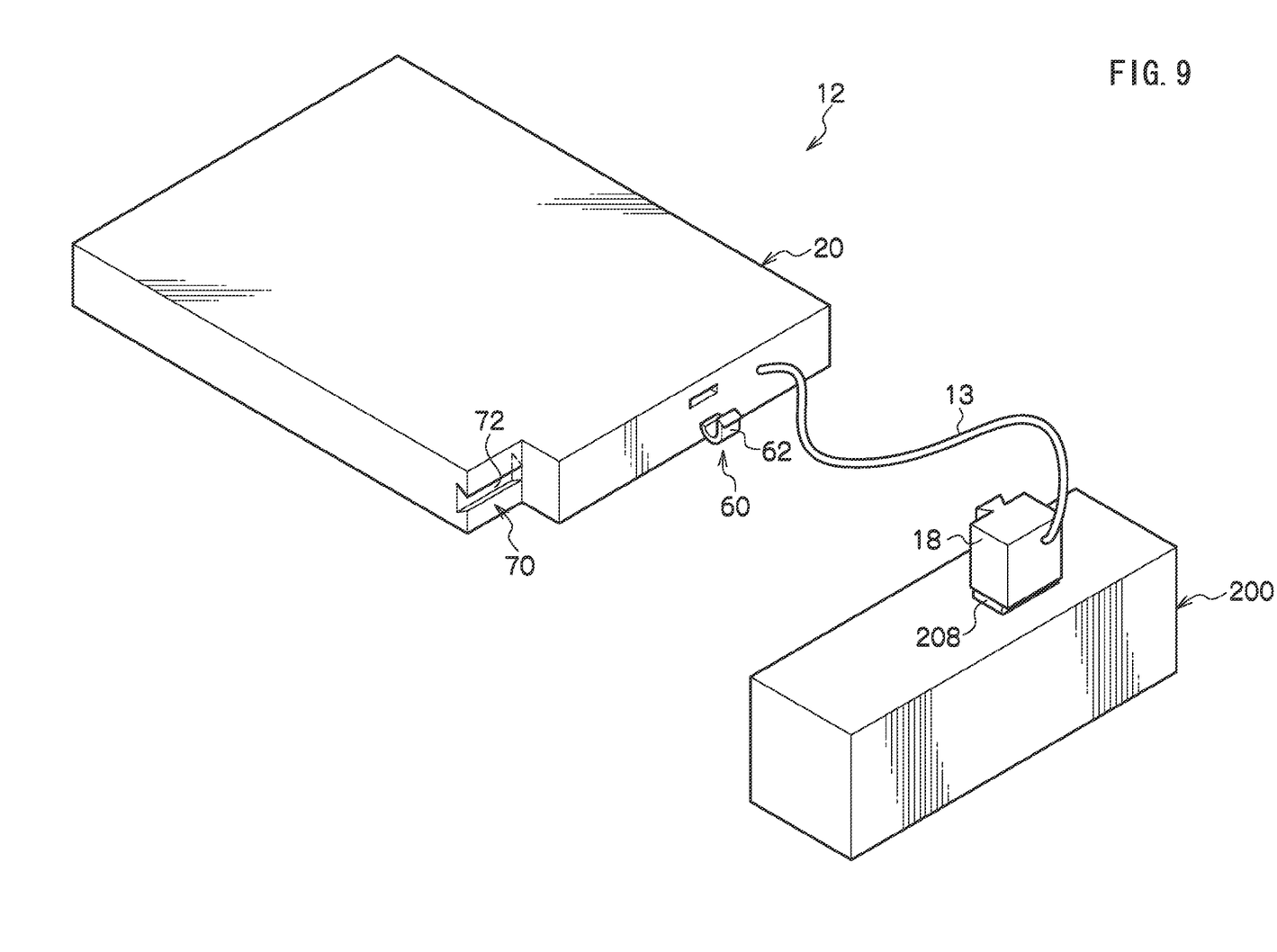
FIG. 9 is a schematic perspective view showing a state in which the connector is connected to a second power supply device.

As shown in FIG. 9, the connector 18 can be connected to the second power supply device 200 in a state in which the connector 18 is removed from the housing 20.

The second power supply device 200 is a portable power supply device, and has a connector 208 to which the connector 18 is connected. The power source 54 can be charged due to the connector 18 being connected to the connector 208 of the second power supply device 200.

In this way, the radiation photographing system of the present exemplary embodiment is structured to include the electronic cassette 12, and the first power supply device 100 and the second power supply device 200 that can charge the electronic cassette 12.

Figure 10A:
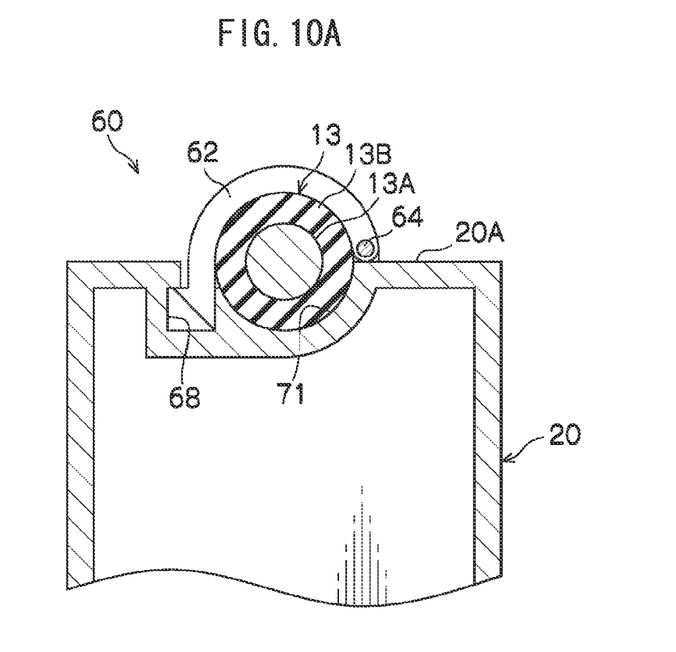
FIG. 10A and FIG. 10B are schematic perspective views showing a holding mechanism that holds a cable at the housing.
Figure 10B:
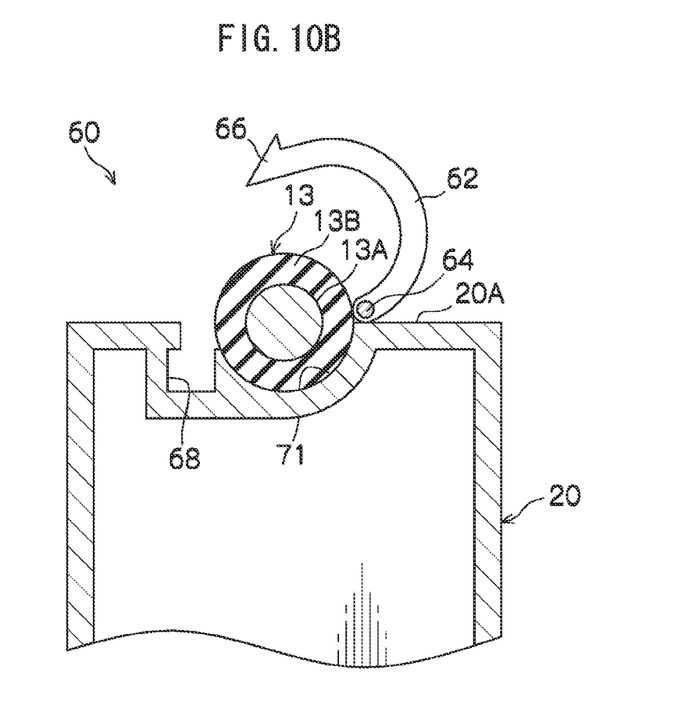

As shown in FIG. 3, FIG. 10A and FIG. 10B, a holding mechanism 60 that holds the cable 13 is provided at the housing 20 along the outer periphery of the housing 20. As shown in FIG. 10A and FIG. 10B, the holding mechanism 60 has a groove 71 that is formed in the side surface 20A, and a holding member 62 that is provided at the side surface 20A of the housing 20.

The groove 71 is formed along a portion of the outer periphery of the cable 13 as shown in FIG. 10A and FIG. 10B. The cable 13 is circular in cross-section, and the groove 71 is formed in a circular arc shape. A portion of the cable 13 is accommodated in the groove 71, and the cable 13 is disposed along the side surface 20A. In the state in which the cable 13 is accommodated in the groove 71, a portion of the outer periphery of the cable 13 projects-out at the outer side of the outer peripheral surface of the housing 20.

The holding member 62 is for holding the cable 13, and is formed in a U-shape (a circular arc shape) along a portion of the outer periphery of the cable 13. One end portion of the holding member 62 is rotatably supported by a shaft 64 provided at the housing 20.

An engaging portion 66 is formed at the other end portion of the holding member 62. An engaging recess 68, with which the engaging portion 66 engages, is formed in the housing 20.

The holding member 62 rotates between an anchored position (refer to FIG. 10A) at which the engaging portion 66 is inserted in and anchored on the engaging recess 68, and a released position (refer to FIG. 10B) at which this anchored state is released.

At the anchored position, the holding member 62 holds the cable 13 that is accommodated in the groove 71. At the released position, the cable 13 can be drawn-out from the housing 20.

Operation of Electronic Cassette 12 Relating to Present Exemplary Embodiment The operation of the electronic cassette 12 relating to the present exemplary embodiment will be described next.

At the electronic cassette 12 relating to the present exemplary embodiment, the cable 13 is held by the holding mechanism 60, and the connector 18 is held by the holding mechanism 70. In this way, in the state in which the cable 13 and the connector 18 are held, the electronic cassette 12 is set in the first power supply device 100, and charging is carried out.

Further, in the state in which the cable 13 and the connector 18 are held, the electronic cassette 12 can be carried, or can be set in a photographing stand, or the like. Moreover, transmission and reception of image data is carried out between the electronic cassette 12 and a display device (not illustrated) by the wireless communication section 52.

Because the electronic cassette 12 can be handled in the state in which the cable 13 and the connector 18 are held in this way, the connector and the cable do not get in the way, and it is easy for the electronic cassette 12 to be handled similarly to a wireless electronic cassette (an electronic cassette without a cable).

Further, at the electronic cassette 12 relating to the present exemplary embodiment, in a case in which charging becomes necessary during the photographing of a radiation image or the like, the connector 18 can be removed from the housing 20 and connected to the second power supply device 200 such that charging can be carried out.

In this way, in cases in which charging becomes necessary immediately, or in cases in which it is troublesome to carry the electronic cassette 12 to the first power supply device 100 and set the electronic cassette 12 in the first power supply device 100 and charge the electronic cassette 12, the electronic cassette 12 can be charged by using the second power supply device 200, without being set in the first power supply device 100.

Further, also in cases in which the sensitivity of the wireless communication is poor or the communication state is poor, wired communication is possible by connecting the connector 18 to the second power supply device 200.

As described above, at the electronic cassette 12 relating to the present exemplary embodiment, in the state in which the connector 18 and the cable 13 are held, the electronic cassette 12 can be handled in the same way as a wireless electronic cassette (an electronic cassette without a cable), and, when needed, the connector 18 can be removed from the housing 20, the cable 13 can be extended, and charging and wired communication can be carried out.

Note that, in the above-described structure, the cable 13 is held at the outer periphery of the housing 20. However, as shown in FIG. 11 through FIG. 14, a take-up mechanism 80, that takes-up the cable 13 at the interior of the housing 20, may be provided.

Figure 11:
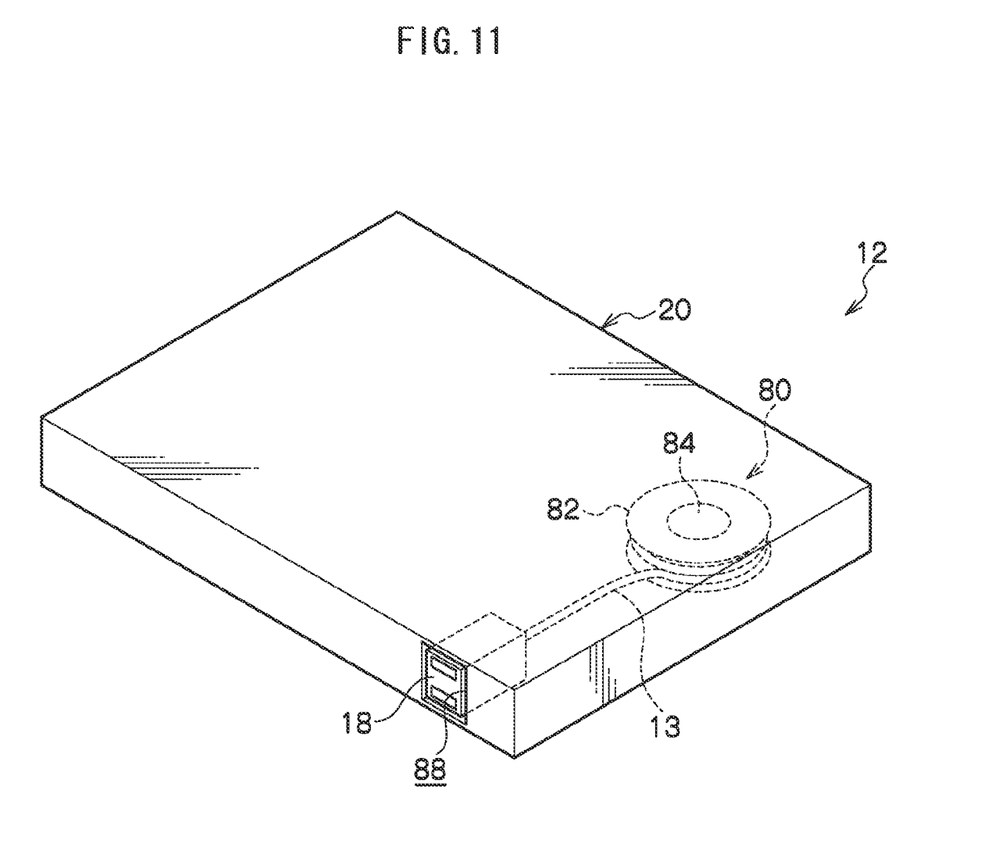
FIG. 11 is a schematic perspective view showing the structure of an electronic cassette equipped with a take-up mechanism that takes-up the cable at the interior of the housing.

The take-up mechanism 80 has a take-up member 82 that takes-up the cable 13. The take-up member 82 is formed in the shape of a disc, and is rotatably supported by a support shaft 84.

Figure 12:
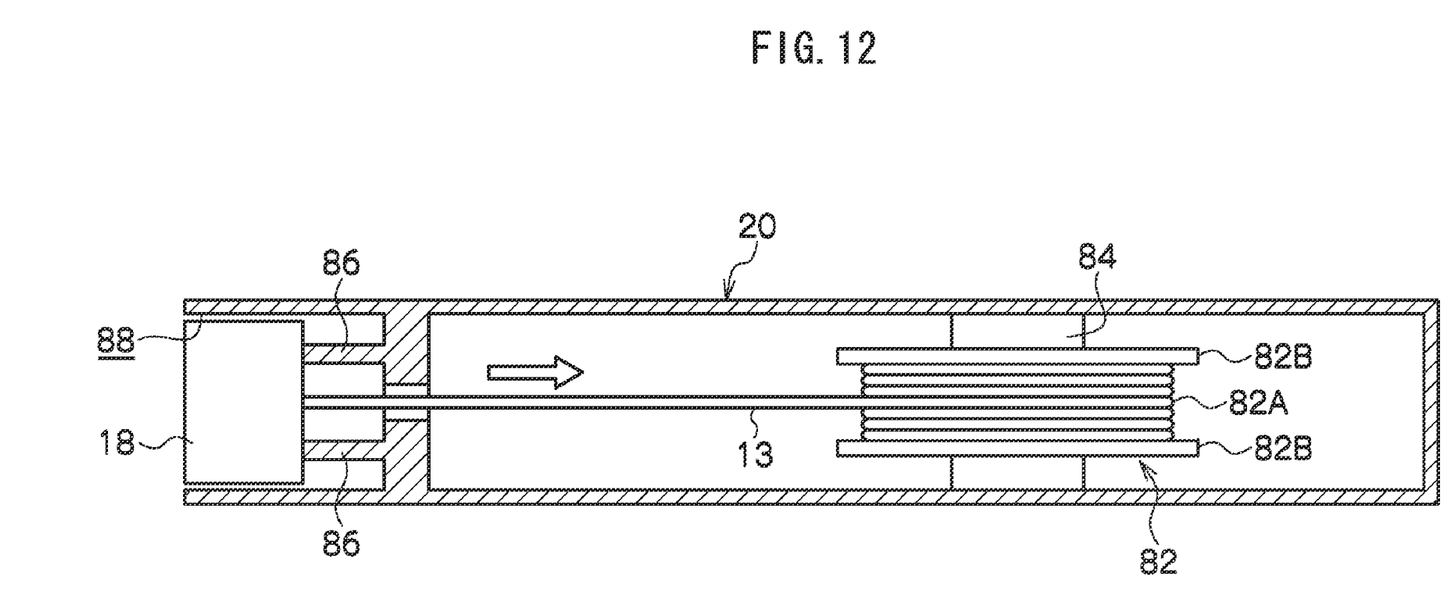
FIG. 12 is a partial sectional view showing the structure of the take-up mechanism.

As shown in FIG. 12, the take-up member 82 has a take-up portion 82A and flanges 82B. The take-up portion 82A is disposed at the central portion in the direction of the rotational axis, and the cable 13 is taken-up therearound. The flanges 82B are disposed at the both ends of the take-up member 82 in the direction of the rotational axis. The take-up member 82 is urged by an urging member (not illustrated) such as a spiral spring or the like in a take-up direction in which the cable 13 is taken-up. A stopper (not illustrated), that stops the rotation of the take-up member 82 and fixes, at an arbitrary drawn-out position, the cable 13 that has been drawn-out from the take-up member 82, is provided at the take-up member 82.

Figure 13:
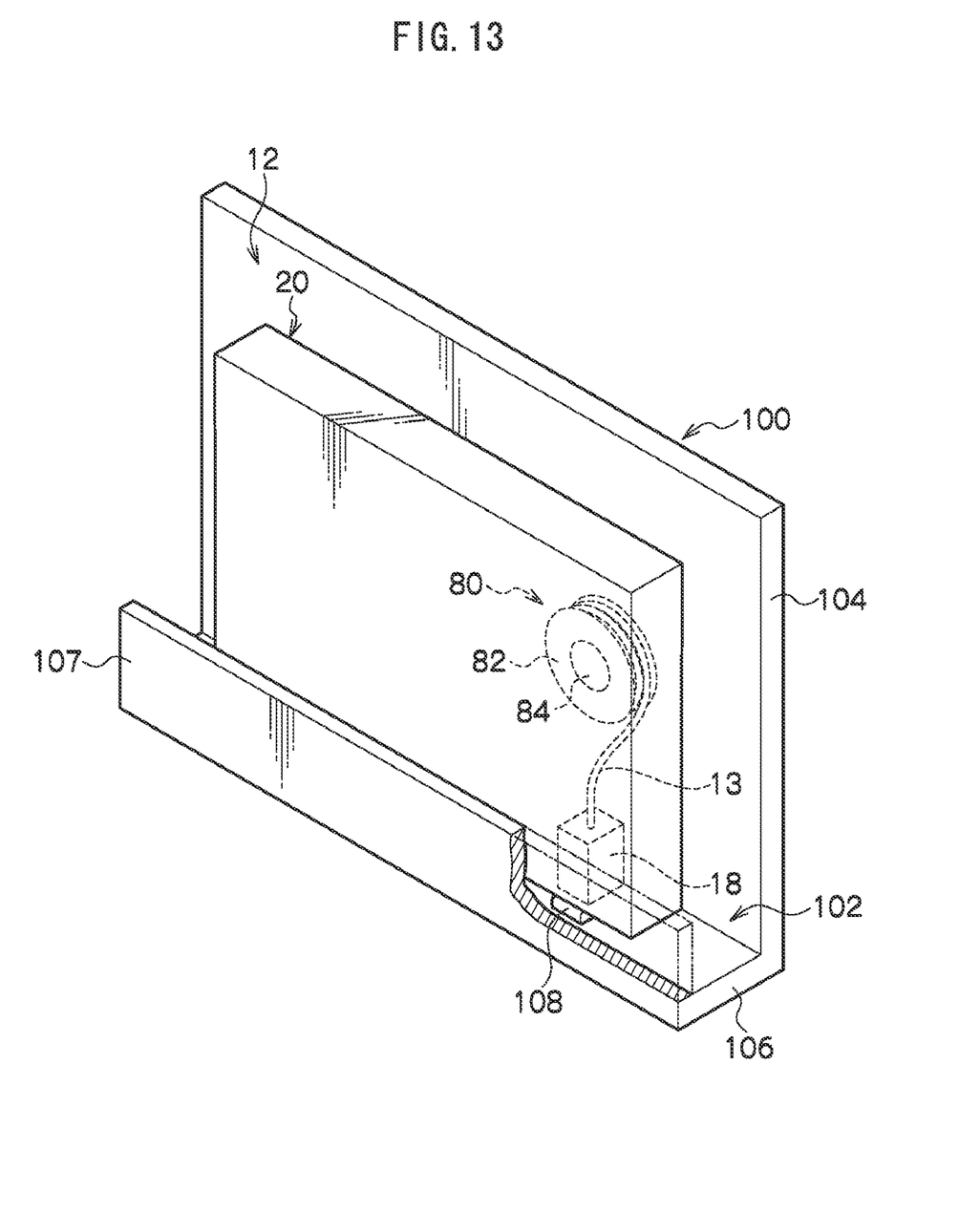
FIG. 13 is a schematic perspective view showing a state in which the connector is connected to the first power supply device, in the structure of the electronic cassette that is equipped with the take-up mechanism.

Further, a holding portion 86, that abuts the connector 18 and removably holds the connector 18 at the housing 20, is formed at the housing 20. In the state in which the connector 18 is held at the housing 20, the connection portion of the connector 18 is exposed at the outer side of the housing 20 through an opening 88 formed in the housing 20. Due thereto, as shown in FIG. 13, by setting the housing 20 in the first power supply device 100, the connector 18 of the electronic cassette 12 and the connector 108 of the first power supply device 100 are connected, and charging of the power source 54 of the electronic cassette 12 is possible.

Figure 14:
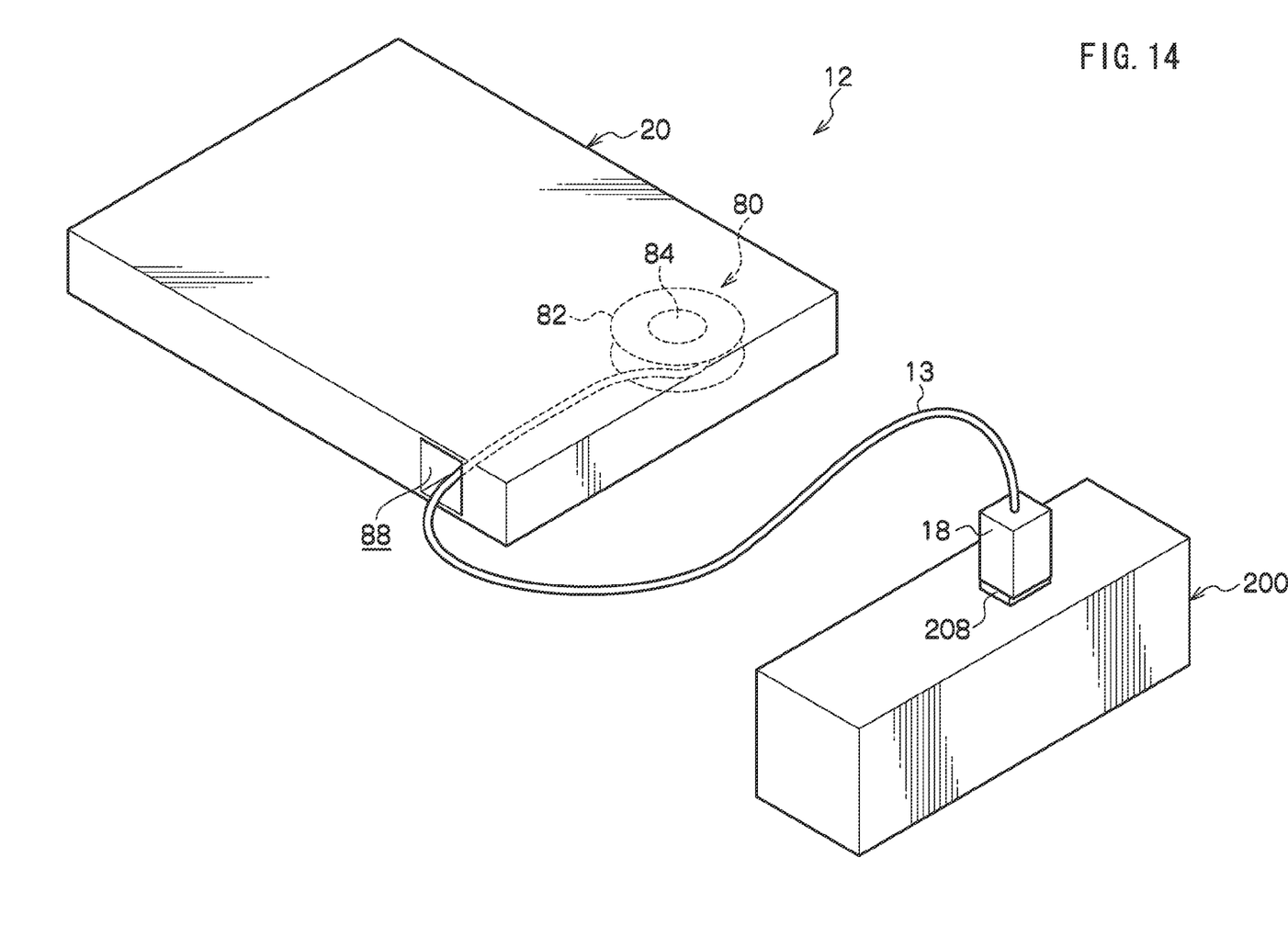
FIG. 14 is a schematic perspective view showing a state in which the connector is connected to the second power supply device, in the structure of the electronic cassette that is equipped with the take-up mechanism.

Further, by drawing-out the cable 13, the connector 18 is removed from the housing 20, and, as shown in FIG. 14, in the state of being removed from the housing 20, the connector 18 can be connected to the second power supply device 200.

In accordance with the portable radiation detector relating to the above-described aspect of the present invention, the image data of the detected radiation image is wirelessly communicated by the wireless communication section. Further, the connector, that is held at the housing by the connector holding mechanism, is removed from the housing, and can be connected to an external device.

Due thereto, if the cable is a cable for electric power supply for example, the portable radiation detector can be charged from an external device. Further, if the cable is a cable for communication, wired communication with an external device is possible.

On the other hand, at times of handling the portable radiation detector (e.g., at times of carrying the portable radiation detector or times of setting the portable radiation detector in a photographing stand), because the connector can be held at the housing, the connector and the cable do not get in the way, and it is easy for the portable radiation detector to be handled similarly to a wireless portable radiation detector (a portable radiation detector without a cable).

In the portable radiation detector relating to the aspect of the present invention, the cable may be a cable for electric power supply, and, due to the housing being set in a first power supply device that is the external device in a state in which the connector is held at the housing, the connector may be connected to the first power supply device.

In accordance with this structure, the connector is connected to the first power supply device due to the housing being set in the first power supply device in a state in which the connector is held at the housing. Due thereto, the portable radiation detector can be charged from the first power supply device.

In this way, because the connector can be connected without removing the connector from the housing, handling of the portable radiation detector is simplified.

In the portable radiation detector relating to the aspect of the present invention, the connector may be able to be connected to a second power supply device that is the external device, in a state in which the connector is removed from the housing.

In accordance with this structure, the connector, that is held at the housing by the connector holding mechanism, is removed from the housing and is connected to second power supply device.

In this way, for example, even if the charge becomes insufficient during photographing of a radiation image, charging can be carried out.

In the portable radiation detector relating to the aspect of the present invention, the cable may also be a cable for carrying out wired communication of the image data, and the portable radiation detector may further include: a wired communication section accommodated in the housing, and carrying out, by the cable and with at least one of the first power supply device and the second power supply device, wired communication of image data of a detected radiation image; and switching section, accommodated in the housing, for switching between the wired communication section and the wireless communication section.

In accordance with this structure, the connector, that is held at the housing by the connector holding mechanism, is removed from the housing and is connected to at least one of the first power supply device and the second power supply device.

Due thereto, even in cases in which the communication state of the wireless communication becomes poor, communication is possible by wired communication.

The portable radiation detector relating to the aspect of the present invention may further include a cable holding mechanism that holds the cable along an outer periphery of the housing.

In accordance with this structure, because the cable can be held along the outer periphery of the housing, the cable does not get in the way, and handling of the portable radiation detector is simplified.

The portable radiation detector relating to the aspect of the present invention may further include a take-up mechanism that takes-up the cable at an interior of the housing.

In accordance with this structure, the cable is taken-up at the interior of the housing. Therefore, the cable does not get in the way, and handling of the portable radiation detector is simplified.

In the present invention, handling of a portable radiation detector having a cable is facilitated.

The present invention is not limited to the above-described exemplary embodiment, and various changes, modifications and improvements can be made thereto.

What is claimed is:

1. A portable radiation detector comprising:
   a housing;
   a wireless communication section accommodated in the housing, to carry out wireless communication of image data of a detected radiation image;
   a cable having one end portion connected to the housing;
   a connector provided at another end portion of the cable, and configured to be connected to an external device; and
   a connector holding mechanism provided at the housing, and holding the connector removably at the housing, wherein the connector is configured to be connected to the external device in a state in which the connector is held at the housing and the housing is set in the external device.

2. The portable radiation detector of claim 1, wherein:
   the cable is a cable for electric power supply; and
   a first power supply device is the external device.

3. The portable radiation detector of claim 2, wherein the connector can be connected to a second power supply device that is the external device, in a state in which the connector is removed from the housing.

4. The portable radiation detector of claim 1, wherein:
   the cable is a cable for electric power supply; and
   the connector can be connected to a second power supply device that is the external device, in a state in which the connector is removed from the housing.

5. The portable radiation detector of claim 3, wherein the cable also serves as a cable for carrying out wired communication of the image data, and the portable radiation detector further comprises:
   a wired communication section accommodated in the housing, to carry out, with the cable and with at least one of the first power supply device or the second power supply device, wired communication of image data of a detected radiation image; and
   a switching section, accommodated in the housing, for switching between the wired communication section and the wireless communication section.

6. The portable radiation detector of claim 1, wherein the cable serves as a cable for carrying out wired communication of the image data, and the portable radiation detector further comprises:
   a wired communication section accommodated in the housing, to carry out, with the cable and with the external device, wired communication of image data of a detected radiation image; and a switching section, accommodated in the housing, for switching between the wired communication section and the wireless communication section.

7. The portable radiation detector of claim 1, further comprising a cable holding mechanism that holds the cable along an outer periphery of the housing.

8. The portable radiation detector of claim 1, further comprising a take-up mechanism that takes-up the cable at an interior of the housing.

* * * * *